United States Patent [19]
Christie et al.

[11] Patent Number: 5,192,329
[45] Date of Patent: Mar. 9, 1993

[54] OBLONG ACETABULAR CUP

[75] Inventors: Michael J. Christie, Nashville, Tenn.; Alfred F. DeCarlo, Jr., Stamford, Conn.; Timothy McTighe, Chagrin Falls, Ohio; Douglas G. Noiles, New Canaan, Conn.

[73] Assignee: Joint Medical Products Corporation, Stamford, Conn.

[21] Appl. No.: 665,952

[22] Filed: Mar. 7, 1991

[51] Int. Cl.⁵ .............................. A61F 2/31
[52] U.S. Cl. ............................................ 623/22
[58] Field of Search .................. 623/18, 19, 22, 23

[56] References Cited

U.S. PATENT DOCUMENTS

| 4,678,472 | 7/1987 | Noiles | 623/22 |
| 4,801,301 | 1/1989 | Noiles | 623/22 |
| 4,883,491 | 11/1989 | Mallory et al. | 623/22 |
| 4,944,759 | 7/1990 | Mallory et al. | 623/22 |
| 4,960,427 | 10/1990 | Noiles | 623/22 |

FOREIGN PATENT DOCUMENTS

| 2516377 | 11/1981 | France | 623/22 |
| 0644511 | 8/1984 | Switzerland | 623/22 |
| 1409051 | 10/1975 | United Kingdom | 623/22 |

OTHER PUBLICATIONS

F. Pipino and P. M. Calderale, "A Biequatorial Acetubular Cup for Hip Prosthesis," *Acta Orthopaedica Belgica*, vol. 48, pp. 5–13 (1980).
F. Pipino and P. M. Calderale, "A Biequatorial Hip Prosthesis," *Panminerva Medica*, vol. 25, pp. 231–239 (1983).

*Primary Examiner*—David Isabella
*Attorney, Agent, or Firm*—Maruice M. Klee

[57] ABSTRACT

An oblong acetabular cup which includes a cavity for receiving a bearing element is provided. The plane of the opening into the cavity is skewed relative to the prosthesis' longitudinal plane so as to achieve adduction correction, anteversion correction, or both adduction and anteversion correction. In certain preferred embodiments, the prosthesis is constructed from two components which can be oriented with respect to one another to achieve different directions and amounts of anteversion correction. In some embodiments, the two components form a cusp in the outside surface of the prosthesis. Surgical instruments and surgical methods for implanting the prostheses are disclosed.

19 Claims, 7 Drawing Sheets

RIGHT SIDE

FIG. 26

LEFT SIDE

OBLONG ACETABULAR CUP

BACKGROUND OF THE INVENTION

1. Field of the Invention

This invention relates to artificial joint prostheses and, in particular, to acetabular prostheses used in hip joint replacements.

2. Description of the Prior Art

Total hip joint replacements comprise a femoral component and an acetabular component. The femoral component is implanted in the patient's femur and the acetabular component is implanted in the acetabular cavity in the patient's pelvis.

Figure 1:
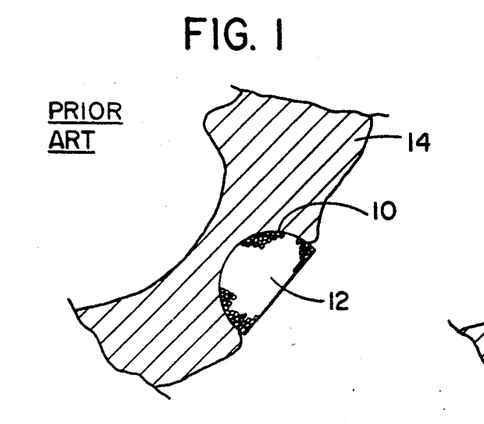
FIG. 1 is a stylized drawing showing the implantation of a spherically-shaped acetabular cup in a spherical cavity formed in a patient's pelvis. The cross-section through the patient's pelvis in this figure and in FIGS. 2, 4, and 6 is in the coronal plane.

The normal acetabular cavity is generally spherically shaped. Accordingly, as illustrated in FIG. 1, during initial hip joint replacement, a spherically-shaped cavity 10 is prepared in the pelvis 14 for the great majority of patients, and the outer surface of the acetabular prosthesis 12 has a generally spherical shape to fit in this cavity. See, for example, Mallory et al., U.S. Pat. Nos. 4,883,491 and 4,944,759.

Figure 2:
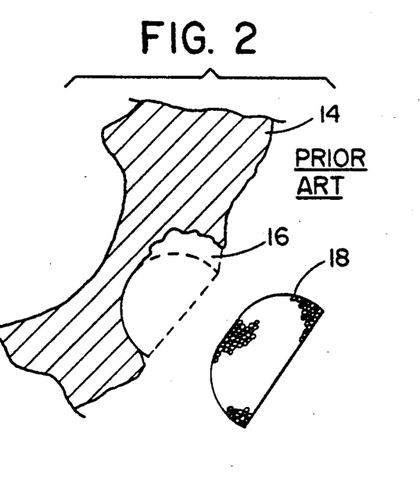
FIG. 2 is a stylized drawing shown an oblong acetabular cup adjacent to a cavity which has become elongated in a posterior and superior direction as a result of the loosening and removal of a prior acetabular prosthesis.
Figure 3:
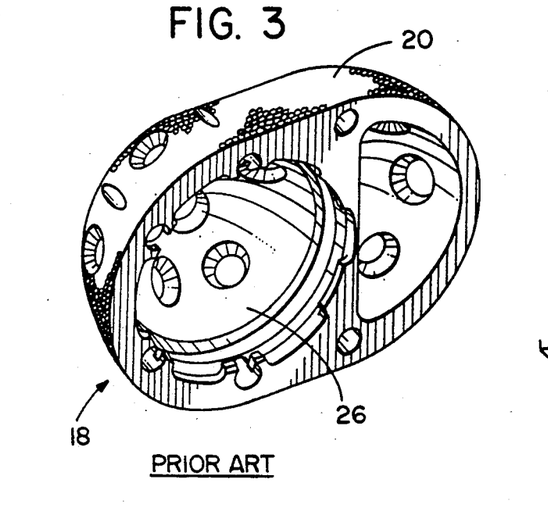
FIG. 3 is a perspective view of a prior art oblong acetabular prosthesis formed from a single block of metal and having no provision for adduction or anteversion correction.

Over the past two decades, millions of hip joint replacements have been performed. As time has progressed, a significant number of these implants have failed by either or both of the femoral or acetabular components becoming loose. In the case of the acetabulum, a loose prosthesis often erodes bone in the direction of the applied forces during use, i.e., in the superior and posterior directions. This is particularly true where the loosened prosthesis had been implanted using bone cement. As a result, during a second or further repeated hip joint replacement, the surgeon often finds that the once spherical cavity in the pelvis has become elongated in a posterior-superior direction, as shown at 16 in FIG. 2 and 32 in FIG. 23. Also, in some cases, elongated acetabular cavities may be found for patients undergoing their first hip joint replacement.

The classical way to deal with this problem of an elongated acetabular cavity has been to fill a portion of the cavity with a bone graft to create as best as possible a spherical cavity in its normal location. As is evident, this approach suffers from a variety of problems, including availability of bone for the bone graft, mechanical difficulties of securing the bone graft to the host bone, failure of the bone graft to provide and maintain long term mechanical support for the prosthesis, and the hazard of the spread of certain infectious diseases.

In some cases, customized elongated or oblong acetabular prostheses have been used to address this condition. FIGS. 2-5 illustrate this approach to the problem. As shown in these figures, a block of metal has been machined to produce prosthesis 18 having outer surface 20 which is composed of two spherical sections 22 connected by a cylindrical section 24. In these custom prostheses, a cavity 26 has been machined in the body of metal to receive a suitable bearing element 28 (see FIG. 4).

Although these oblong prostheses have represented an improvement over the bone graft approach, they have suffered from a number of problems of their own. First, they have been expensive to manufacture because a separate machining setup has been required for each prothesis geometry which has been produced. As a result, oblong prostheses of this construction have been used in only a limited number of cases.

Figure 4:
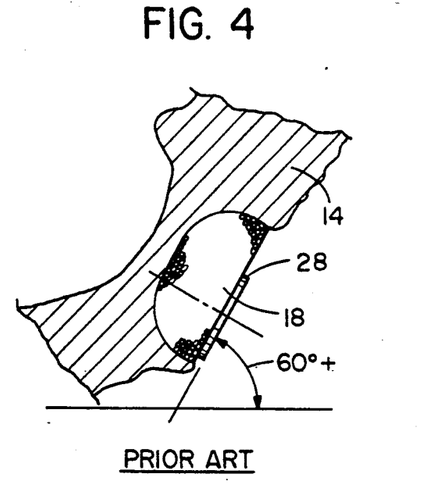
FIG. 4 is a stylized drawing showing the implantation of a prior art prosthesis of the type shown in FIG. 3. As illustrated in this figure, the angle between the face of bearing 28 and the transverse plane is 60° or more, which is undesirable.
Figure 5:
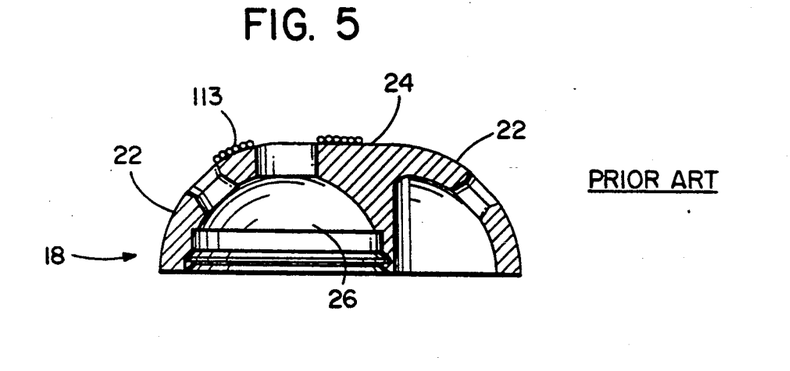
FIG. 5 is a cross-sectional view through the longitudinal axis of the prosthesis of FIG. 3.

Even more importantly, the existing oblong prostheses have not fully responded to the anatomical and physiological needs of the patient. This problem is illustrated in FIG. 4. As shown in this figure, the angle in the coronal plane (X-Z plane in FIG. 17) between the face of the bearing element 28 of the prior art oblong prostheses and the transverse plane (X-Y plane in FIG. 17) is typically 60 or more degrees. This orientation results from the contour of the bone and the elongation of the cavity. In medical terminology, the prosthesis is said to have an insufficient amount of adduction, i.e., the angle between the face of the prosthesis and the transverse plane is greater than the preferred angle. (Note that the amount of adduction increases as the angle decreases.)

Figure 19:
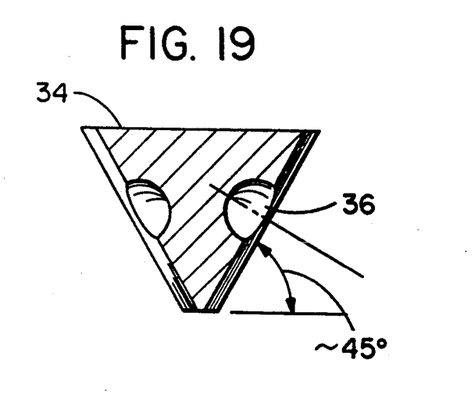
FIG. 19 is a coronal (X-Z) section along lines 19—19 in FIG. 18 showing the desired adduction angle of approximately 45° for an acetabular prosthesis.

For joint stability, however, the preferred angle of the face of the bearing element in the coronal plane is on the order of 45 degrees or less. See F. Pipino and P.M. Calderale, "A Biequatorial Acetabular Cup for Hip Prosthesis," *Acta Orthopaedica Belgica*, Vol. 48, pages 5-13 (1980) and F. Pipino and P.M. Calderale, "A Biequatorial Hip Prosthesis," *Panminerva Medica*, Vol. 25, pages 231-239 (1983). See also FIG. 19. Thus, the configuration of FIG. 4 is typically more than 15° from the preferred orientation. Moreover, the greater the elongation of the cavity, the greater the departure from the preferred orientation. In terms of function, such a geometry means that the patient will have a significantly higher likelihood of dislocation during use.

Figures 17, 18:
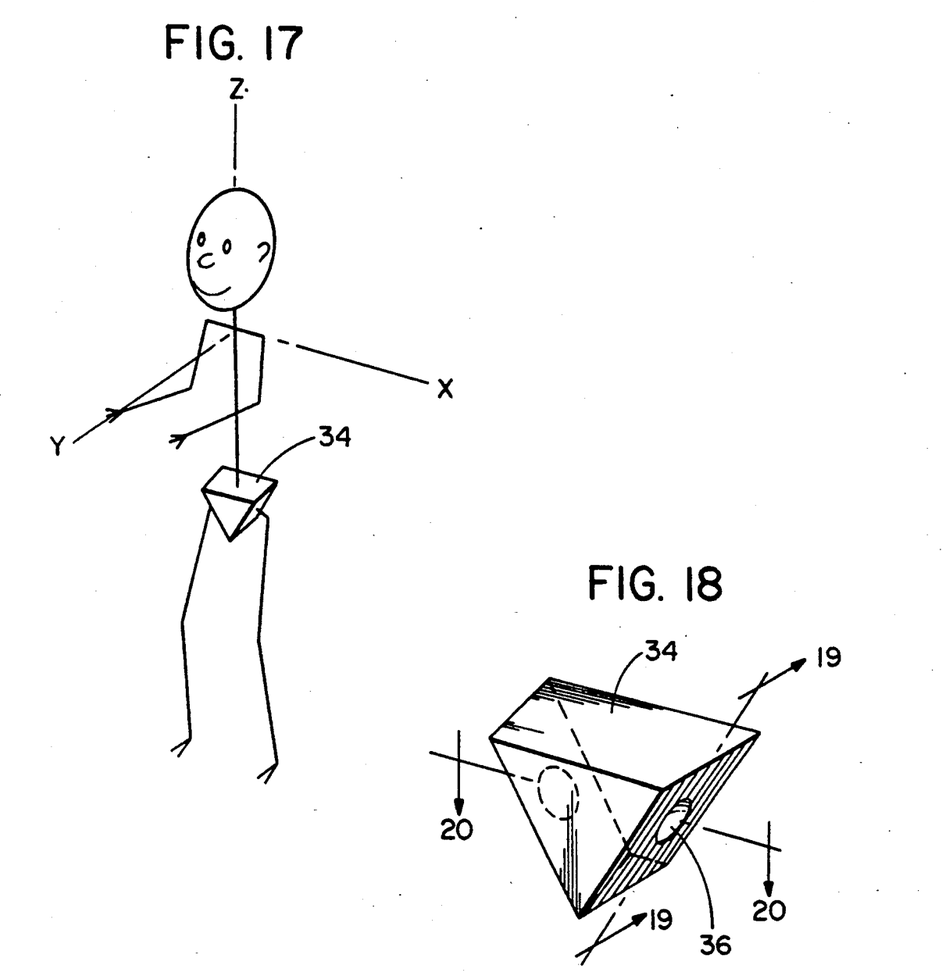
FIG. 17 is a stylized, perspective view of a person showing the coronal (X-Z), transverse (X-Y) and sagittal (Y-Z) planes. A stylized portrayal of the person's pelvis is shown at 34.
FIG. 18 is an enlarged view of the stylized pelvis 34. A stylized portrayal of the normal acetabulum is shown at 36.
Figure 20:
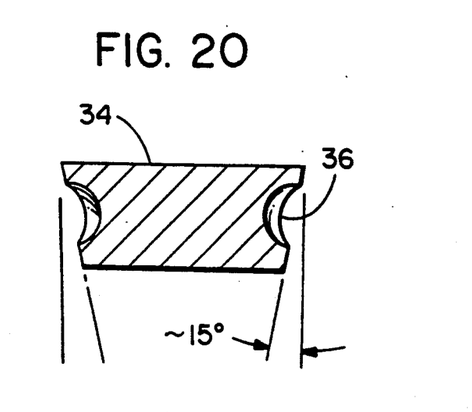
FIG. 20 is a transverse (X-Y) section along lines 20—20 in FIG. 18 showing the desired anteversion angle of approximately 15° for an acetabular prosthesis.

In addition to the orientation in the coronal plane, the functionality of the prosthesis is also affected by the orientation of the face of the bearing element in the transverse plane (X-Y plane in FIG. 17). In this case, the preferred angle between the face of the bearing element and the sagittal plane (Y-X plane in FIG. 17) is on the order of 15° anteverted. See FIG. 20. (Note that the amount of anteversion increases as the angle increases.)

Due to the curvature of the pelvis and the usual direction of erosion and elongation, the prior art oblong acetabular prostheses tend to assume an orientation which is less anteverted or, in some cases, may even be retroverted. The magnitude of this problem also becomes greater as the elongation of the cavity becomes greater. Again, in terms of function, orientations which are less anterverted or are retroverted mean that the patient will have a higher likelihood of dislocation during use.

Figure 6:
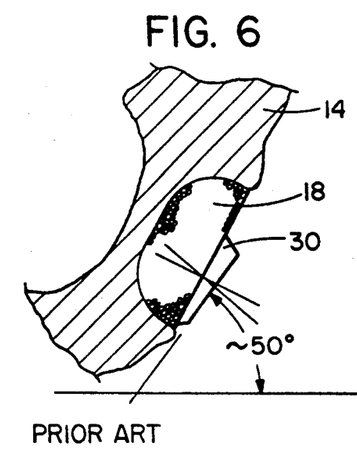
FIG. 6 is a stylized drawing showing the implantation of a prior art prosthesis of the type shown in FIG. 3 equipped with a bearing element 30 having a skewed face. The angle between the face of bearing element 30 and the transverse plane is approximately 50° which is better than the 60+° of FIG. 4, but is still unsatisfactory.

An alternative construction is shown in FIG. 6 wherein an asymmetric bearing element 30 having a skewed face is used. For a skew which is orientable (see Noiles U.S. Pat. No. 4,678,472), some compensation can be made for the misorientation in both the coronal and transverse planes. FIG. 6 shows a typical improvement in the coronal plane. As shown in this figure, skewing the face of the bearing element can bring the angle in the coronal plane down to around 50°. However, full correction cannot be satisfactorily achieved in this way because a sufficiently large extension of the plastic bearing would be mechanically inadequate to withstand the loads applied during use. Similarly, some improvement in inadequate anteversion can be achieved in the transverse plane, but again full correction cannot be achieved without jeopardizing the mechanical strength of the bearing.

SUMMARY OF THE INVENTION

In view of the foregoing state of the art, it is an object of the present invention to provide improved oblong acetabular prostheses. More particularly, it is an object of the invention to provide oblong acetabular prostheses which more adequately respond to the anatomical and physiological needs of the patient. Specifically, it is an object of the invention to provide oblong acetabular prostheses in which the prosthesis' bearing element can be placed in a preferred orientation in either or both of the coronal and transverse planes without putting the mechanical integrity of the bearing element at risk.

It is a further object of the invention to provide a method for efficiently and economically manufacturing oblong acetabular prostheses having the above attributes.

It is an additional object of the invention to provide surgical instruments and surgical methods for implanting oblong acetabular prostheses having the above attributes.

To achieve the foregoing and other objects, the invention in accordance with certain of its aspects provides an oblong acetabular cup which defines a longitudinal plane and which comprises a body which includes a cavity for receiving a bearing element, said cavity having an opening which defines a first plane, said first plane intersecting the longitudinal plane at an angle such that when the prosthesis is implanted, the first plane has an orientation in the patient's body which is:

(a) more adducted than the orientation of the longitudinal plane; or (b) more anteverted than the orientation of the longitudinal plane; or (c) both more adducted and ore anteverted than the orientation of the longitudinal plane.

In accordance with another of its aspects, the invention provides an oblong acetabular cup comprising:

(a) a first component having (i) a cavity for receiving a bearing element and (ii) an outer surface at least a portion of which is adapted for engagement with bone, said portion being generally spherically-shaped about a first center;

(b) a second component having an outer surface at least a portion of which is adapted for engagement with bone, said portion being generally spherically-shaped about a second center, said second component being constructed separately from the first component; and (c) means for joining the first and second components together with the first and second centers displaced from one another.

In accordance with certain preferred embodiments of these aspects of the invention, the means for joining comprises cylindrically-shaped surfaces on the first and second components which engage and mate with one another in the assembled prosthesis. This construction is particularly well-suited for the manufacture of prostheses which include anteversion correction because 1) the cylindrically-shaped surfaces allow the first and second components to be joined to one another with the first component rotated relative to the second component by different amounts thus allowing for different amounts of anteversion correction, and 2) the ability of the first and second components to mate at different rotational angles allows right-handed and left-handed prostheses to be manufactured from a common set of components.

Depending upon the locations and sizes of the cylindrically-shaped surfaces used to join the first and second components, the outside, bone-engaging surface of the oblong prosthesis can include two spherically-shaped portions at either end and a central, cylindrically-shaped portion or can include two spherically-shaped portions which meet with one another to form an inwardly-directed cusp in the prosthesis' outside surface.

In accordance with others of its aspects, the invention provides apparatus and a surgical method for forming a cavity having two, adjacent, spherically-shaped portions accurately spaced from one another. The thusly-formed cavity can include a ridge of bone which can engage a cusp in the outside surface of the prosthesis when the prosthesis is constructed to have such a cusp.

In accordance with the surgical method, a first spherical cavity is cut in the patient's pelvis following which a second spherical cavity is cut which may partially overlap the first cavity so as to produce an oblong cavity having a cusp-shaped ridge of bone at the junction between the two spherical cuts. To allow the second cavity to be accurately positioned relative to the first cavity, the invention provides a surgical instrument which comprises:

(a) guide means for engaging the surface of a first spherical cavity;

(b) cutting means for cutting a second spherical cavity; and (c) means for holding the guide means and the cutting means in a predetermined spatial relationship.

The accompanying drawings, which are incorporated in and constitute part of the specification, illustrate the preferred embodiments of the invention, and together with the description, serve to explain the principles of the invention. It is to be understood, of course, that both the drawings and the description are explanatory only are are not restrictive of the invention.

DESCRIPTION OF THE PREFERRED EMBODIMENTS

Figure 7:
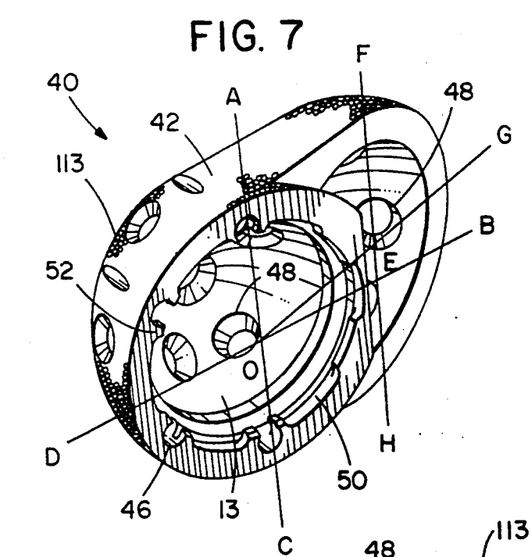
FIG. 7 is a perspective view of a prosthesis constructed in accordance with the present invention from a single block of metal and having a bearing-receiving cavity which has been skewed to provide adduction correction.
Figure 8:
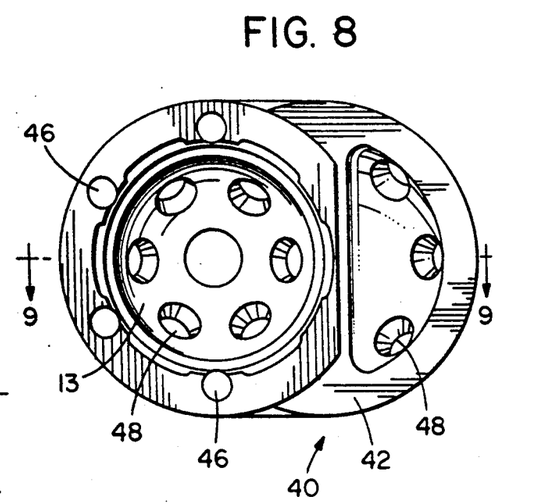
FIG. 8 is a plan view of the prosthesis of FIG. 7.
Figure 9:
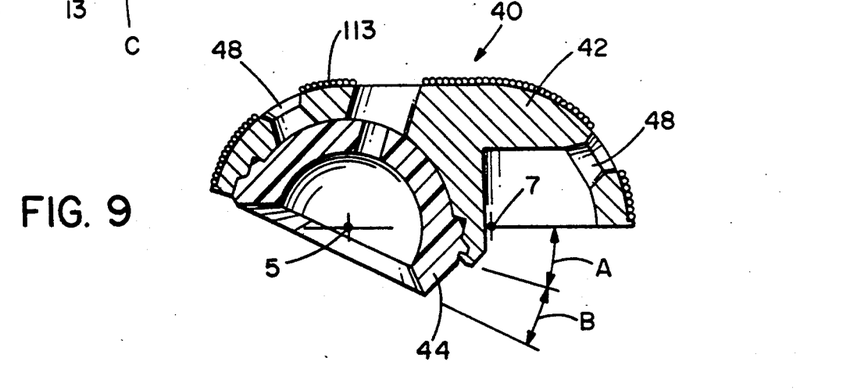
FIG. 9 is a cross-sectional view along lines 9—9 in FIG. 8 of the prosthesis of FIG. 7 with a skewed bearing element inserted into the prosthesis' skewed cavity. The centers of the two spherically-shaped portions of the outside surface of the cup are identified by the reference numbers 5 and 7.

With reference now to the drawings, wherein like reference characters designate like or corresponding parts throughout the several views, there is shown in FIGS. 7-9 an oblong acetabular cup 40 constructed in accordance with the present invention.

As shown in these figures, the prosthesis is made from a single block of material, e.g., a block of metal, and includes body 42 in which is formed cavity 13 for receiving bearing element 44. In addition to bearing-receiving cavity 13, body 42 also includes apertures 48 which 1) allow the surgeon to visualize the underlying bone as the prosthesis is implanted and 2) can receive bone screws for affixing the prosthesis to the pelvis.

Bearing 44 is retained in cavity 13 by means of 1) complimentary bayonet spaces 50 and lugs 52 formed at the mouth of the cavity which receive and mate with corresponding spaces and lugs formed on the outside surface of the bearing, and 2) bone screws (not shown) which pass through apertures 46 and lock the bearing to the prosthesis. See Noiles U.S. Pat. Nos. 4,801,301 and 4,960,427. Other means for securing the bearing to the cup can of course be used, if desired.

As shown in FIG. 7, prosthesis 40 has a longitudinal axis defined by line OEG and a longitudinal plane which is defined by lines OEG and FEH and which contains line AOC. For the particular construction shown, points O and E are the centers of two spherically-shaped surfaces which form the ends of the oblong cup.

The opening into bearing-receiving cavity 13 defines a "first" plane which contains lines AOC and DOB. In accordance with the invention, the opening into cavity 13 and thus the first plane is skewed with respect to the prosthesis' longitudinal plane so as to provide adduction correction or anteversion correction or both adduction correction and anteversion correction.

The prosthesis of FIGS. 7-9 shows the case of adduction correction only. The first plane is rotated out from the longitudinal plane by adduction correction angle GOB in FIG. 7 which is also shown as angle A in FIG. 9. The magnitude of the adduction correction angle will generally be in the range of from about 10° to about 30°, although larger or smaller adduction correction angles can be used for particular applications if necessary or desired. Prostheses having adduction correction angles of different magnitudes can be provided to the surgeon so that a selection can be made at the time of implantation to better meet the needs of individual patients. For example, the surgeon can be given a choice between prostheses having adduction correction angles of 10, 20, and 30 degrees.

As shown in FIG. 7, the first plane and the longitudinal plane intersect along line AOC. Because only adduction correction is being performed, this line of intersection is perpendicular to the longitudinal axis of the oblong prosthesis, i.e., line AOC is perpendicular to line OEG. As discussed below, when both adduction and anteversion correction is performed, the angle between the longitudinal axis and the line of intersection is greater than 90° for a right hip cup and less than 90° for a left hip cup. When only anteversion correction is performed, the line of intersection between the first plane and the longitudinal plane is the longitudinal axis or, in the general case, is parallel to that axis.

FIG. 9 shows the use of skewed bearing element 44 with cup 40. This combination allows for even greater adduction correction, i.e., correction through the sum of angles A and B in FIG. 9. Also, by using an orientable bearing (see Noiles U.S. Pat. No. 4,678,472), some anteversion correction can be achieved for a cup having only adduction correction. Conversely, the use of an orientable, skewed bearing allows some adduction correction for a cup having only anteversion correction.

Further, by using an orientable, skewed bearing with a cup having both adduction and anteversion correction, relatively fine adjustments of the levels of adduction and anteversion correction can be made in situ. This allows the surgeon to achieve as good a match as possible between the configuration of the prosthesis and the needs of the patient. In particular, it gives the surgeon the needed flexibility to address the twin goals of maximum range of motion and minimum likelihood of dislocation. It is important to note that by skewing the opening to cavity 13, bearing 44 has strong mechanical support from the body of the cup even though the bearing's orientation is substantially different from that of the cup's longitudinal plane/axis.

Figures 10, 11, 12:
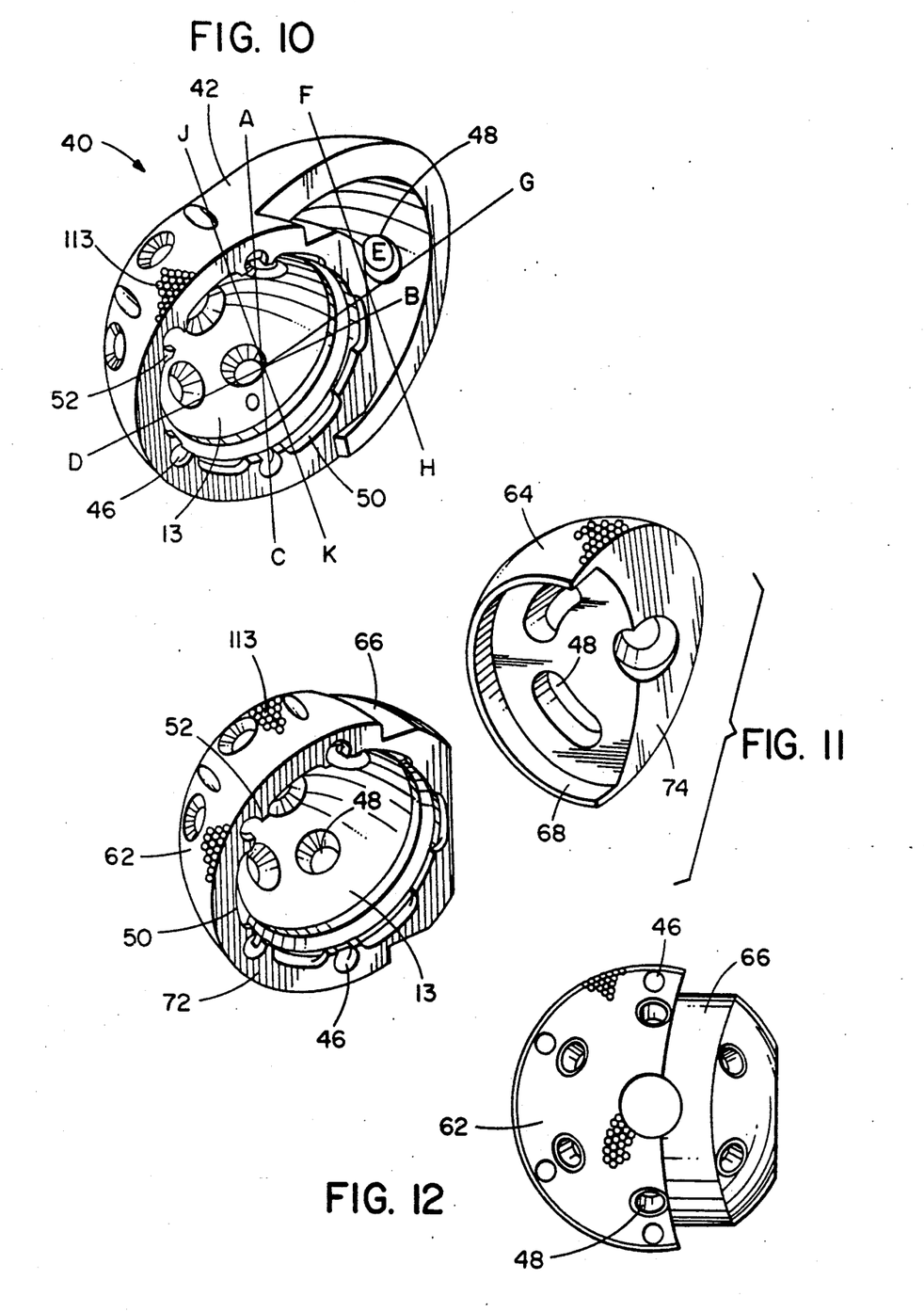
FIG. 10 is a perspective view of a prosthesis constructed in accordance with the present invention from a single block of metal and having a bearing-receiving cavity which has been skewed to provide both adduction and anteversion correction.
FIG. 11 is an exploded, perspective view of a prosthesis constructed in accordance with the present invention from two components which when united produce an outside surface for the prosthesis which includes a cusp.
FIG. 12 is a plan view of the cavity-containing component of the prosthesis of FIG. 11.

FIG. 10 shows an oblong cup having both adduction and anteversion correction. As in FIG. 7, points O and E are the centers of two spherically-shaped surfaces which form the ends of the oblong cup. Also, as in FIG. 7, the longitudinal axis of the cup of FIG. 10 is defined by line OEG, the longitudinal plane of the cup is defined by lines OEG and FEH, the first plane contains lines AOC and DOB, and the adduction correction angle is GOB. In this case, however, the longitudinal plane does not contain line AOC, but rather contains the reference line JOK which is parallel to the reference line FEH. The angle between lines AOC and JOK, i.e., angle JOA, represents the anteversion correction angle for this cup.

The magnitude of the anteversion correction angle will generally be in the range of from about 10° to about 30°, although larger or smaller anteversion correction angles can be used for particular applications if necessary or desired. As with the adduction correction angle, prostheses having anteversion correction angles of different magnitudes, e.g., prostheses having anteversion correction angles of 10, 20, and 30 degrees, can be provided to the surgeon.

Figure 24:
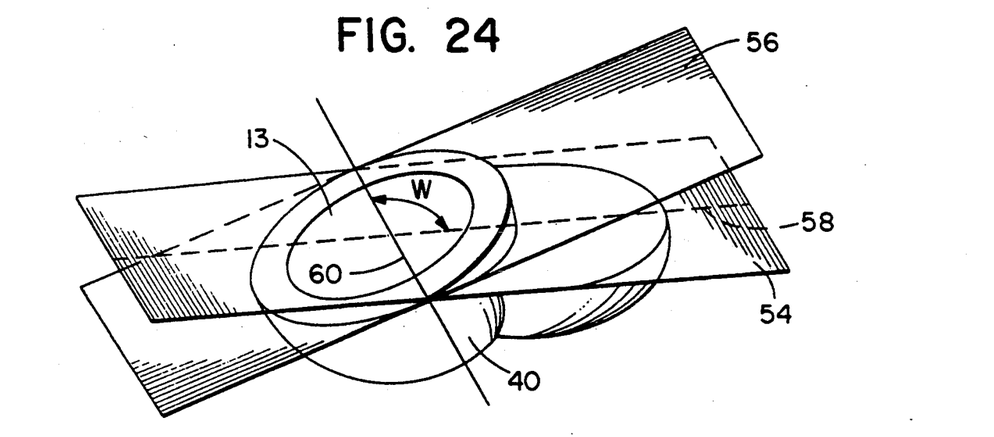
FIGS. 24-26 are stylized view of the prostheses constructed in accordance with the present invention showing the prostheses' longitudinal plane and the plane defined by the opening of the prosthesis' bearing-receiving cavity. The prosthesis of FIG. 24 includes only adduction correction and thus can be used in either the patient's right or left hip. The prostheses of FIGS. 25 and 26 include both adduction and anteversion correction and thus can be advantageously used in the right hip for the FIG. 25 prosthesis and the left hip for the FIG. 26 prosthesis.
Figure 25:
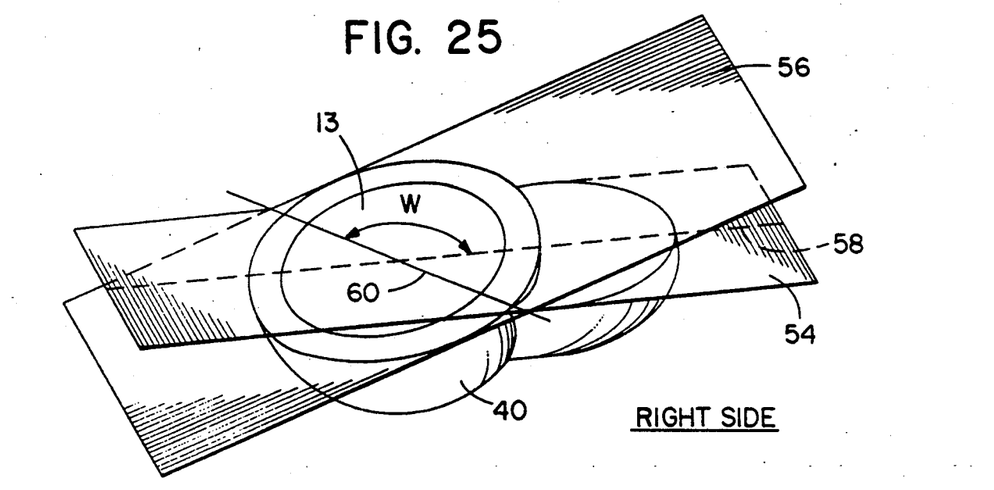
Figure 26:
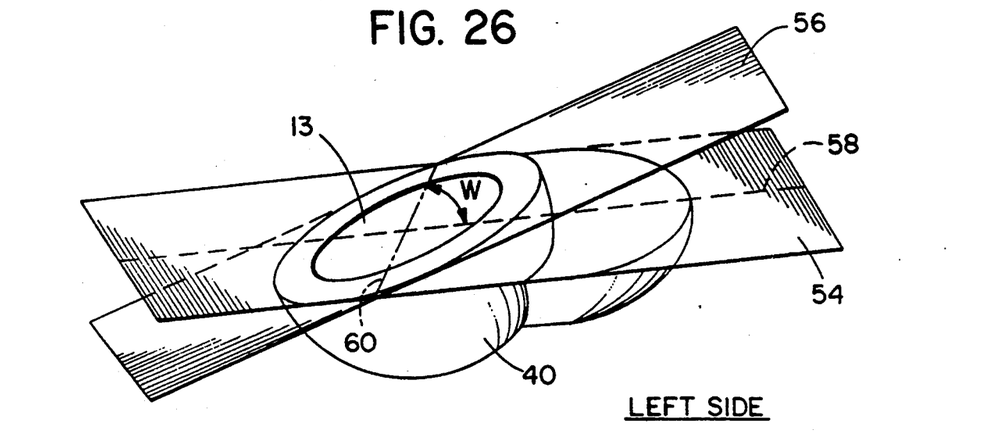

Since anteversion corrections are in relation to the patient's midsagittal plane, different prostheses are needed for the right and left hips. Specifically, for a right hip, the first plane is rotated to the patient's left relative to the prosthesis' longitudinal plane, while for the left hip, it is rotated to the right. This effect is shown in FIGS. 25 and 26, where 54 is the prosthesis' longitudinal plane, 56 is the first plane, 58 is the prosthesis' longitudinal axis, and 60 is the line of intersection between the first plane and the longitudinal plane. For comparison, FIG. 24 shows a prosthesis having only adduction correction.

The prosthesis of FIG. 25, like that of FIG. 10, is for a right hip and thus first plane 56 is rotated to the left relative to longitudinal plane 54. The FIG. 26 prosthesis, on the other hand, is for a left hip and thus first plane 56 has been rotated to the right relative to the longitudinal plane. This aspect of the invention can also be seen by examining the angle W between the prosthesis' longitudinal axis 58 and the line of intersection 60 between the first plane and the longitudinal plane. As shown in FIG. 25, for a right hip, angle W is greater than 90°, while as shown in FIG. 25, for a left hip, it is less than 90°. For comparison, as shown in FIG. 24, for a prosthesis with just adduction correction and no anteversion correction, angle W equals 90°.

FIGS. 11-13 and 14-16 show particularly preferred constructions for the prostheses of the present invention. In each case, body 42 of the prosthesis is composed of two components which engage and mate with each other along cylindrically-shaped surfaces. In this way, anteversion corrections of different magnitudes and right and left hip prostheses can be easily constructed from a common set of components by simply joining the components together at different offset angles.

Figure 13:
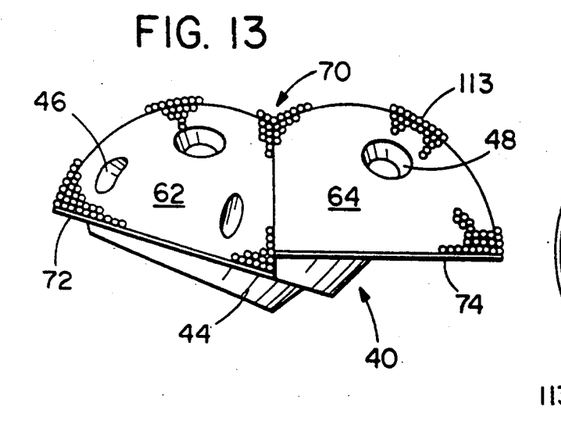
FIG. 13 is a side view of the assembled prosthesis of FIG. 11.

In FIGS. 11-13, component 62 includes bearing-receiving cavity 13 and component 64 extends away from components 62 to produce the overall oblong shape of the cup. The outside, bone-engaging surfaces of both components are portions of a sphere. Accordingly, when the components are joined together, the outside surface of the assembled cup includes cusp 70 at the intersection between the two spherical portions.

The overall length of the cup can be adjusted by varying the size of component 64, i.e., by using more or less of a sphere to form the outside surface of this component. Also, the outside surfaces of the components can have different spherical radii to provide further flexibility in the overall configuration of the cup. As shown most clearly in FIG. 13, face 72 of component 62 meets face 74 of component 64 at an angle so as to provide the assembled prosthesis with adduction correction.

Components 62 and 64 are joined together by means of cylindrically-shaped external surface 66 on component 62 and cylindrically-shaped internal surface 68 on component 64. To produce anteversion correction, the components are rotated relative to one another along these surfaces. When the desired degree and direction of anteversion correction has been selected, the components are permanently joined together by, for example, electron beam welding in a vacuum in the case of metal components.

Figure 21:
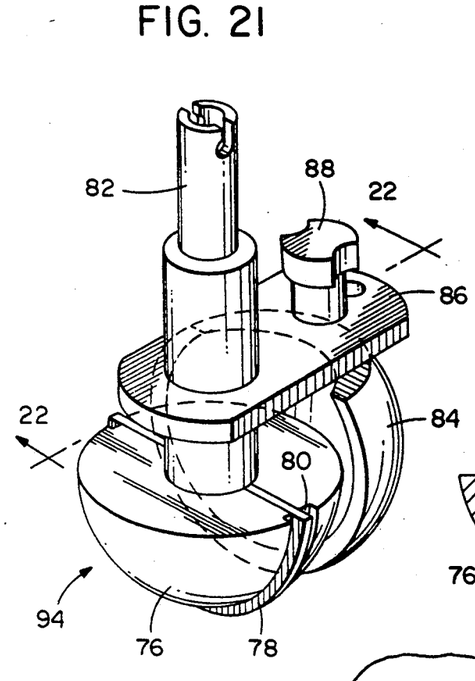
FIG. 21 is a perspective view of a surgical instrument for use in implanting the prostheses of the present invention.
Figure 22:
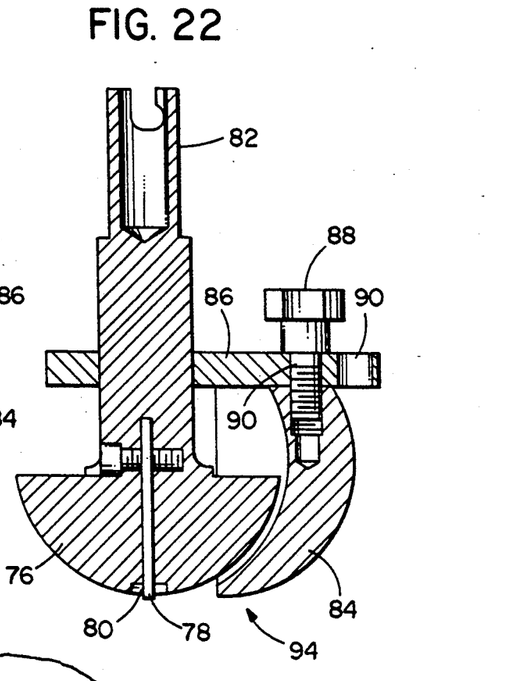
FIG. 22 is a sectional view along lines 22—22 of the surgical instrument of FIG. 21.

As mentioned above, the prosthesis of FIGS. 11-13 includes cusp 70 in its outside surface. A surgical instrument 94 suitable for preparing a cavity in a patient's pelvis for receiving such a prosthesis is shown in FIGS. 21 and 22. Instrument 94 comprises spherical shell 84 and spherical reamer 76, which includes cutting blade 78 and chip clearance groove 80. The reamer is driven by conventional means (not shown) through shaft 82.

Extending out from shaft 82 is platform 86 to which is attached shell 84. As explained below, the shell serves as a guide for cutting a second spherical cavity in the patient'pelvis adjacent to a first spherical cavity. The radii of reamer 76 and shell 84 correspond to the radii of the bone-engaging surfaces of components 64 and 62, respectively. Accordingly, the reamer and the shell can have different radii if components 64 and 62 have different radii.

Platform 86 includes holes 90 through which threaded bolt 88 can pass to attach shell 84 to the platform. Multiple holes are provided so that instrument 94 can be used with prostheses of different sizes, e.g., prostheses having larger and smaller components 64. Although only two adjustments are shown, more adjustments can, of course, be provided if a greater variety of prostheses is to be made available to the surgeon.

Figure 23:
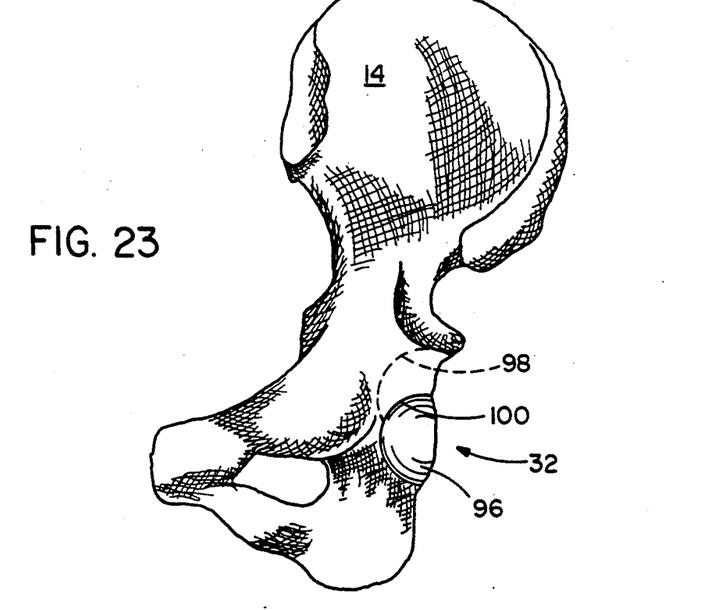
FIG. 23 is a perspective view of a portion of a human pelvis showing the cavity formed in the pelvis through the use of the instrument of FIG. 21.

The implantation of a prosthesis using the instrument of FIGS. 21 and 22 is illustrated in FIG. 23. First, the surgeon prepares first spherical cavity 96 using a conventional reamer. Next, the surgeon cuts second spherical cavity 98 using instrument 94. Specifically, the surgeon places shell 84 into the first spherical cavity and uses the shell as a guide to cut the second cavity at a predetermined distance from the first cavity. The result is finished cavity 32 which includes a ridge of bone 100 which will mate with cusp 70 in the outside surface of the prosthesis.

Figures 14, 16:
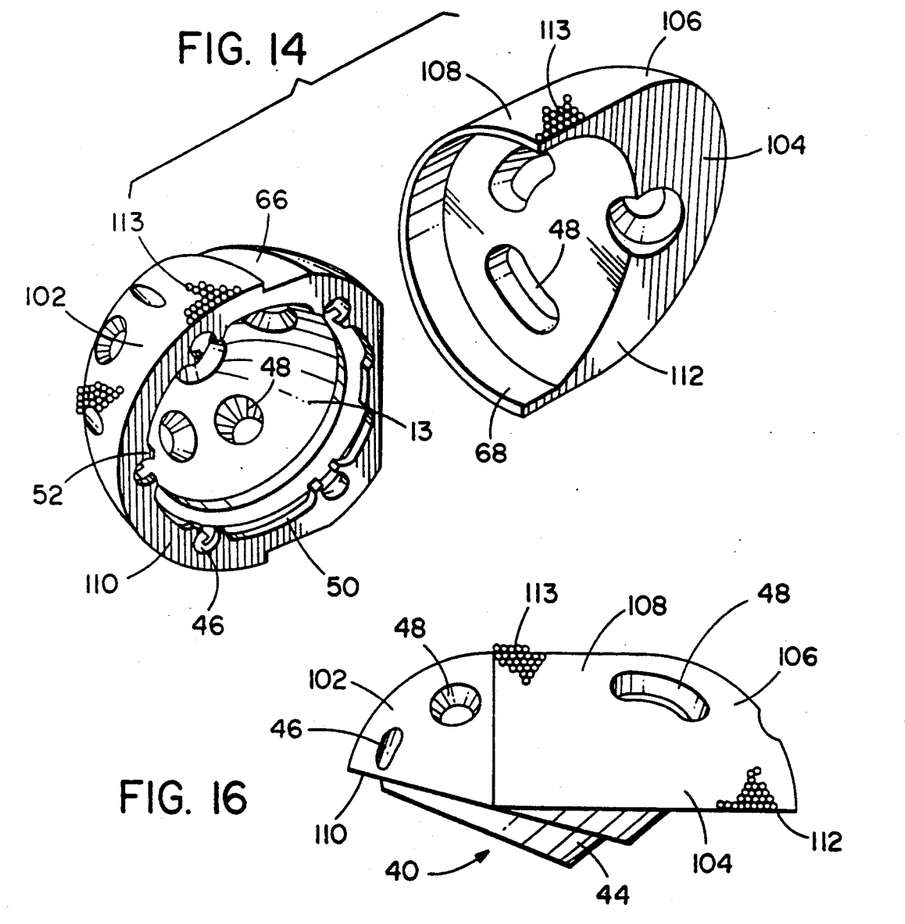
FIG. 14 is an exploded, perspective view of a prosthesis constructed in accordance with the present invention from two components which when united produce an outside surface for the prosthesis which has a central cylindrical portion.
FIG. 16 is a side view of the prothesis of FIG. 14.
Figure 15:
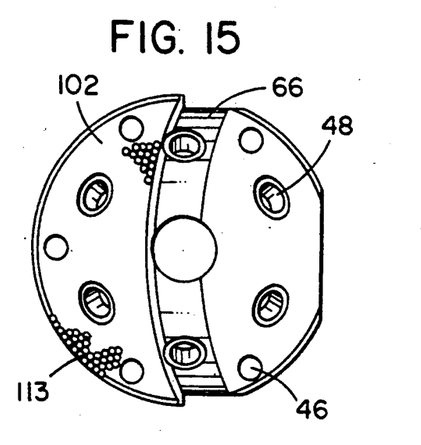
FIG. 15 is a plan view of the cavity-containing component of the prosthesis of FIG. 14.

FIGS. 14–16 show a second two-component embodiment of the invention, again using cylindrically-shaped surfaces 66 and 68 at the interface between the components to allow for easy anteversion correction. In this case, component 102 includes bearing-receiving cavity 13 and component 104 extends away from component 102 to produce the overall oblong shape of the cup.

The outside, bone-engaging surface of component 102 is a portion of a sphere, while the outside, bone-engaging surface of component 104 includes a spherical portion 106 and a cylindrical portion 108. For this embodiment, adjustments in the overall length of the prosthesis can be easily made by simply changing the length of cylindrical portion 108. As shown most clearly in FIG. 16, face 110 of component 102 meets face 112 of component 104 at an angle so as to provide the assembled prosthesis with adduction correction.

The embodiment of FIGS. 14–16 has two, spaced-apart, outside, spherically-shaped surfaces, and thus an instrument of the type shown in FIGS. 21 and 22 can advantageously be used to produce a cavity in the patient's pelvis for this prosthesis as described above. Because the prosthesis does not include a cusp, a conventional reamer is advantageously used to form a continuous cylindrical connection between the spaced-apart, spherically-shaped sections of the cavity resulting from the use of instrument 94. The finished cavity thus includes two spherically-shaped portions and a cylindrically-shaped portion corresponding to the outside surface of the prosthesis.

The prostheses of the invention are preferably implanted by being press fit into the prepared cavity in the patient's bone. Bone screws which pass through screw holes 48 can be used to provide additional fixation for the prosthesis. Preferably, the outside surface of the prosthesis includes porous coating 113 to provide long term fixation through bone ingrowth. To provide a tight initial fit between the prosthesis and the prepared cavity, the prosthesis with its porous coating is dimensioned approximately 1 millimeter larger in diameter than the cavity.

The prostheses of the invention can be made of conventional materials known in the art for making artificial joint replacements. For example, the body of the cup can be made of a Ti 6Al 4V alloy, the porous coating can be chemically pure titanium, and the bearing can be ultra high molecular weight polyethylene. Other materials now known or subsequently developed can of course be used in the practice of the invention. Similarly, the prostheses of the invention can be manufactured using conventional techniques known in the art such as through the use of computer controlled machine tools.

Although specific embodiments of the invention have been described and illustrated, it is to be understood that modifications can be made without departing from the invention's spirit and scope. For example, the outside surface of the prosthesis can have configurations other than those shown, a variety of instruments other than that shown in FIGS. 21 and 22 can be used to prepare a cavity for the prosthesis, and methods different from those illustrated can be used to join together the various part of the prosthesis.

Along these same lines, the geometry of the prosthesis can be described in terms different from those used above. For example, the prosthesis can be described in terms of the shape of its outer surface and the central axis of the cavity which receives the bearing element.

As discussed above, the prosthesis' outer surface includes two spherically-shaped portions, the centers of which spheres are spaced-apart and thus define a line. In the prior art oblong prostheses, the central axis of the bearing-receiving cavity was perpendicular to the line between the centers of the spheres. In contrast, in accordance with the present invention, when adduction correction is performed, the central axis intersects the line between the centers at an angle other than 90°.

A variety of other variations and modifications which do not depart from the scope and spirit of the invention will be evident to persons of ordinary skill in the art from the disclosure herein. The following claims are intended to cover the specific embodiments set forth herein as well as such modifications, variations, and equivalents.

What is claimed is:

1. An acetabular cup for implantation in a patient's pelvis comprising a body having:
   (a) a first outer surface for engagement with bone,
   (b) a second outer surface having an overall oblong configuration which defines a longitudinal plane and a longitudinal axis, and
   (c) a cavity formed in the body for receiving a bearing element,
said cavity having an opening formed in a portion of said second outer surface which defines a first plane, said first plane forming an acute angle with said longitudinal plane in a direction along the longitudinal axis such that when the acetabular cup is implanted in the patient's pelvis said first plane is more adducted than the longitudinal plane.

2. The acetabular cup of claim 1 wherein the first plane forms an acute angle with said longitudinal plane in a direction transverse to the longitudinal axis such that when the acetabular cup is implanted in the patient's pelvis, said first plane is more anteverted than the longitudinal plane.

3. An acetabular cup for implantation in a patient's pelvis comprising a body having:
   (a) a first outer surface for engagement with bone,
   (b) a second outer surface having an overall oblong configuration which defines a longitudinal plane and a longitudinal axis, and
   (c) a cavity formed in the body for receiving a bearing element,
said cavity having an opening formed in a portion of said second outer surface which defines a first plane, said first plane forming an acute angle with said longitudinal plane in a direction transverse to the longitudinal axis such that when the acetabular cup is implanted in the patient's pelvis said first plane is more anteverted than the longitudinal plane.

4. An acetabular cup comprising a body having:
   (a) a first outer surface for engagement with bone,
   (b) a second outer surface having an overall oblong configuration which defines a longitudinal plane and a longitudinal axis, and
   (c) a cavity formed in the body for receiving a bearing element,
said cavity having an opening formed in a portion of said second outer surface which defines a first plane, said first plane intersecting said longitudinal plane at an angle greater than 0°.

5. The acetabular cup of claim 4 wherein the angle between the longitudinal axis and the line of intersection between the first plane and the longitudinal plane is equal to 90°.

6. The acetabular cup of claim 4 wherein the angle between the longitudinal axis and the line of intersection between the first plane and the longitudinal plane is greater than 90°.

7. The acetabular cup of claim 4 wherein the angle between the longitudinal axis and the line of intersection between the first plane and the longitudinal plane is less than 90°.

8. The acetabular cup of claim 1 wherein the first outer surface comprises a first portion which is generally spherically-shaped about a first center and a second portion which is generally spherically-shaped about a second center which is displaced from the first center.

9. The acetabular cup of claim 8 wherein the first and second portions have substantially equal radii.

10. The acetabular cup of claim 8 wherein the first and second portions meet one another to form a cusp.

11. The acetabular cup of claim 8 wherein the first outer surface further comprises a generally cylindrically-shaped portion which connects the first and second portions.

12. The acetabular cup of claim 3 wherein the first outer surface comprises a first portion which is generally spherically-shaped about a first center and a second portion which is generally spherically-shaped about a second center which is displaced from the first center.

13. The acetabular cup of claim 12 wherein the first and second portions have substantially equal radii.

14. The acetabular cup of claim 12 wherein the first and second portions meet one another to form a cusp.

15. The acetabular cup of claim 12 wherein the first outer surface further comprises a generally cylindrically-shaped portion which connects the first and second portions.

16. An acetabular cup comprising a body having:
  (a) a first outer surface for engagement with bone,
  (b) a second outer surface having an overall oblong configuration which defines a longitudinal plane and a longitudinal axis, and
  (c) a cavity formed in the body for receiving a bearing element,
said cavity having an opening formed in a portion of said second outer surface which defines a first plane, said first plane forming an acute angle with said longitudinal plane.

17. The acetabular cup of claim 16 wherein the acute angle is in a direction along the longitudinal axis.

18. The acetabular cup of claim 16 wherein the acute angle is in a direction transverse to the longitudinal axis.

19. The acetabular cup of claim 16 wherein the first plane forms an acute angle with the longitudinal plane both in a direction along and in a direction transverse to the longitudinal axis.

* * * * *